United States Patent [19]

Kuhn et al.

[11] 4,110,428

[45] Aug. 29, 1978

[54] ANTIPERSPIRANT COMPOSITION

[75] Inventors: Johannes Andries Kuhn, Illovo Beach; Randolph James Wilkinson, Durban North, both of Natal, South Africa

[73] Assignee: Lever Brothers Company, New York, N.Y.

[21] Appl. No.: 713,775

[22] Filed: Aug. 12, 1976

Related U.S. Application Data

[63] Continuation of Ser. No. 525,267, Nov. 19, 1976, abandoned, which is a continuation-in-part of Ser. No. 124,453, Mar. 15, 1971, abandoned.

[30] Foreign Application Priority Data

Mar. 23, 1970 [GB] United Kingdom ............... 13827/70

[51] Int. Cl.$^2$ .......................... A61K 9/14; A61K 7/32
[52] U.S. Cl. ......................................... 424/46; 424/47; 424/68
[58] Field of Search ............................ 424/47, 68, 46

[56] References Cited

U.S. PATENT DOCUMENTS

| 2,872,379 | 2/1959 | Neuman et al. ....................... 424/47 |
| 2,890,987 | 6/1959 | Hilfer .................................... 424/68 |
| 3,395,214 | 7/1968 | Mummert ............................... 424/47 |
| 3,509,253 | 4/1970 | Babbin .................................. 424/47 |
| 3,555,146 | 1/1971 | Jones .................................... 424/47 |
| 3,579,465 | 5/1971 | Schmolka ........................... 424/66 X |
| 3,634,480 | 1/1972 | Sheffield ............................... 424/47 |
| 3,767,786 | 10/1973 | Kilmer et al. ...................... 424/66 X |

FOREIGN PATENT DOCUMENTS

| 1,167,173 | 10/1969 | United Kingdom ...................... 424/47 |
| 940,279 | 1963 | United Kingdom ...................... 424/47 |

OTHER PUBLICATIONS

Harry Cosmetic Materials, 1963, vol. 2, pp. 352-357.
Chem. Abs., vol. 54, p. 13538i.

*Primary Examiner*—Dale R. Ore
*Attorney, Agent, or Firm*—James J. Farrell; Melvin H. Kurtz; Michael J. Kelly

[57] ABSTRACT

An aerosol antiperspirant composition of the type in which an antiperspirant agent such as aluminium chlorhydrate is suspended in a propellant medium, the medium containing a polyalkylene glycol for example a butoxymonoether of an ethylene oxide — propylene oxide condensate, an ethylene oxide — propylene oxide block copolymer or a polypropylene glycol. The effect of including a polyalkylene glycol is to substantially reduce the amount of stain which develops on clothing to which the antiperspirant becomes accidentally transferred.

1 Claim, No Drawings

ANTIPERSPIRANT COMPOSITION

This is a continuation, of application Ser. No. 525,267, filed Nov. 19.1974, now abandoned which is in turn a continuation-in-part of our application Ser. No. 124,453, filed Mar. 15, 1971 now abandoned.

This invention relates to antiperspirant compositions, particularly to those of the powder suspension type suitable for spraying from a pressurised container.

Aerosol compositions containing a propellant and a finely divided astringent compound, often impalpable aluminum chlorhydrate, which is insoluble in the propellant are widely known. For example they are disclosed in British Pat. specification No. 1,167,173. Such compositions conventionally contain a fatty substance such as a fatty acid ester, for example isopropyl myristate, which helps to maintain the antiperspirant compound in stable suspension or dispersion.

We have observed a disadvantage of this type of antiperspirant composition, namely that on repeated application, clothing in contact with areas of the body which have been sprayed, or clothing which has itself become sprayed accidentally, develops a stain. In a test which we have used to monitor the amount of stain produced by various formulations of antiperspirant compositions, the formulation is sprayed onto a cotton sheet, allowed to dry, and washed. The procedure is then repeated. Products which are referred to herein as non-staining do not produce a stain even after 5 cycles of the test, which is described fully elsewhere.

Generally staining is more pronounced in the warmer climates and with users who perspire freely: for instance, we have noticed heavy staining on shirts, brassieres or blouses worn in the heat of the summer in South Africa.

Our experiments indicate that the staining effect is largely due to build-up of the fatty substance used as a suspending/dispersing agent and we have now discovered that this can be mitigated.

We have found that a substantial reduction in the level of staining on clothing contacted repeatedly with antiperspirants can be achieved by incorporating into the antiperspirant compositions certain polyalkylene glycols.

According to the invention, therefore, there is provided an antiperspirant composition having a reduced tendency to stain clothing comprising an antiperspirant agent in the form of an astringent salt of a multivalent cation suspended in a solution of a colourless water- and propellant-miscible polyalkylene glycol as herein defined in an aerosol propellant.

The term "polyalkylene glycol" is defined as meaning a polyglycol formed from an alkylene oxide such as ethylene oxide or propylene oxide, or a monoalkyl ether thereof, having a viscosity of from about 60 to about 1500 centipoises at 25° C.

The polyglycols may be formed in general by reacting the required alkylene oxide or mixture of alkylene oxides with a hydroxylic substance such as water, a lower alkylene glycol, for example ethylene glycol or propylene glycol, or a lower aliphatic alcohol such as butyl alcohol.

The requirement that the viscosity of the glycol should be from about 60 to about 1500 centipoises at 25° C excludes from the definition such oligomeric glycols as tetraethylene glycol which has a viscosity of 44 centipoises at 25° C.

The term polyalkylene glycol thus includes not only simple polyalkylene glycols such as polypropylene glycols but also alkyl monoethers thereof such as the substances supplied by the Union Carbide Corporation under the Trade Mark "Ucon".

The Ucon fluids and lubricants are described in the pamphlet "Ucon fluids and lubricants" published by Union Carbide Corporation, 270 Park Avenue, New York, USA in 1968, which is incorporated herein by reference.

As is stated in this pamphlet, the Ucon fluids which are water soluble are in the 50 HB (sometimes called HB) and the 75-H (sometimes called H) series, and it is these series which are useful for the purposes of this invention.

The pamphlet also states that the number which follows the series symbol 50HB or 75-H designates the viscosity of the fluid in Saybolt Universal Seconds at 100° F. We prefer to use Ucons 50-HB-660, 50-HB-2000 and 50-HB-3520 or mixtures thereof and so this is equivalent to saying that we prefer to use Ucon fluids having viscosities of from about 660 to about 3520, although fluids having viscosities outside this range, for example Ucon 50-HB-400 may also be used. Additionally Ucon fluids having viscosities lower than those mentioned above may be used in conjunction with major proportions of higher viscosity fluids so that the viscosity of the mixture falls within the preferred range.

Of the two fluids available in the 75 H series, we prefer to use the higher viscosity one, Ucon 75-H-1400 although this too, may be used in conjunction with a lower viscosity fluid such as Ucon 75-H-450 or with one or more of the fluids in the 50-HB series.

Other physical properties of Ucon 50-HB and 75-H fluids are described in the pamphlet referred to above.

The preparation and chemical properties of Ucon fluids are described in U.S. Pat. No. 2,425,755 which is incorporated herein by reference. As stated in that specification the fluids, which are aliphatic ethers of polyoxyalkylene glycols, can be prepared by the addition to a monohydric aliphatic alcohol, of a mixture of ethylene oxide and 1,2 propylene oxide according to the equation:-

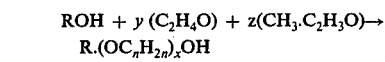

$$\text{ROH} + y(C_2H_4O) + z(CH_3.C_2H_3O) \rightarrow R.(OC_nH_{2n})_xOH$$

where $y$ and $z$ represent the number of moles of ethylene oxide and 1,2-propylene oxide respectively which are used in the reaction relative to the number of moles of alcohol used, $n$ is 2 or 3 and $x$ is $y + z$.

In the Ucon 50-HB series of fluids mentioned above, the monohydroxy aliphatic alcohol is butanol.

Polyalkylene oxide adducts of monohydric alcohols are well known in the art. It is well known in the art that adducts containing a large proportion of ethylene oxide units are not soluble in the common halogenated hydrocarbon aerosol propellants and it would be well understood that such adducts would be unsuitable for use in this invention, which requires that the polyalkylene glycol should be miscible with the propellant.

Polypropylene glycols have also been found to be suitable for use in the compositions of this invention. The polypropylene glycols are well known substances in the cosmetic art and are described in the pamphlet "Dow Polypropylene Glycols" published in 1960 by the Dow Chemical Company, Midland, Michigan, USA, which is incorporated herein by reference and also in Cosmetic Materials, Vol. 2 by R. G. Harry, published by Leonard Hill (Books) Limited, London in 1963, pages 356 and 357 of which are also incorporated herein by reference.

Polypropylene glycols are formed by the action of propylene oxide on propylene glycol or water. The products having average molecular weights of from about 400 to about 2,000 are clear liquids which are soluble in water and it is these polypropylene glycols which we prefer to use in the compositions of this invention, particularly low polypropylene glycols 425, 1025 and 2025.

A third group of preferred polyalkylene glycols for use in this invention are the block copolymers of ethylene oxide and propylene oxide having the general formula $$HOC_2H_4(C_2H_4O)a(C_3H_6O)b(C_2H_4O)c\ C_2H_4OH$$

where a, b and c are integers.

These are well known to those skilled in the art and are described on pages 350 and 351 of "Cosmetic Materials" Vol.2 referred to above. These pages are incorporated herein by reference.

The block copolymers are prepared by first forming a polypropylene glycol of molecular weight 900 to 2,500 by the condensation of propylene oxide with propylene glycol or water. These polyglycols are then made to react with ethylene oxide so that a long polyoxyethylene chain is added on at each end of the polypropylene glycol.

These block copolymers are available from the Wyandotte Chemicals Corporation under the Trade Mark "Pluronic". The physical properties of the various different copolymers are described in the pamphlet "Pluronics", published by the suppliers. We have found Pluronics L62D, L121 and L64 to be most useful in the compositions of our invention.

As already mentioned, conventional powder-suspension type aerosol antiperspirants generally contain a fatty suspending/dispersing agent which maintains an insoluble salt in suspension/dispersion. The polyalkylene glycols of the present invention may be added to conventional antiperspirant compositions either as a substitute for, or in addition to these fatty suspending agents, although we have found greater stain alleviation to be produced if the fatty substance is eliminated entirely.

In general, the main components of aerosol antiperspirants according to the invention are an antiperspirant agent, a germicide, a polyalkylene glycol, an auxiliary suspending agent and an aerosol propellant.

The antiperspirant agents suitable for incorporation in the compositions of the invention are those which are insoluble in the liquid medium of the aerosol composition which consists largely of a mixture of fluorinated hydrocarbons. Examples of antiperspirant agents are aluminium chlorhydrate, which is preferred, and other astringent aluminium salts such as aluminium chloride, aluminium sulphate and aluminium sulphocarbonate; astringent salts of multivalent cations, for example zinc chloride, zinc sulphate and zinc sulphocarbonate and zirconium salts such as zirconium tetrachloride and zirconium sulphate.

Typical germicides for use in the compositions of the invention are halogenated phenols such as hexchlorophene, dichlorophene, tetrachlorophene and dithionol, quaternary ammonium compounds such as alkyldimethyl benzyl ammonium chloride an cetyltrimethyl ammonium bromide, phenolic compounds such as methylisopropyl phenols, Lysol, p-hydroxybenzoic acid esters and chlorinated germicides such as chloramine T.

Typical auxiliary suspending agents are hydrophobic clays such as Bentone 34 (Trade Mark) a reaction product of bentonite and dimethyl distearyl ammonium chloride; colloidal zinc silicas such as Cab-O-Sil M-S (Trade Mark) a submicroscopic particulate silica prepared in a hot gas environment by the vapour phase hydrolysis of a silicon compound, Aerosil 200 (Trade Mark) a pyrogenic silica and Santocel 54 (Trade Mark) and grease forming soaps such as aluminium stearate.

The aerosol propellants used in the composition of the invention may be chosen from, for example, hydrocarbons such as n-propane, isopropane, butane and isobutane and halogenated hydrocarbons such as fluorotrichloromethane (Freon 11), difluorodichloromethane (Freon 12), fluorodichloroethane (Freon 114), pentafluorochloroethane (Freon 115), methylene chloride and vinyl chloride, and mixtures thereof. The vapour pressure should, in general be chosen so as to provide a vapour pressure in the range of 15 to 75 psig at 70° F. "Freon" is a Trade Mark.

Typical ingredients of the compositions to which the invention may be applied are: from 0.1 to 10% of an antiperspirant agent which is insoluble in the aerosol propellant, from 0.02 to 0.5% to a bacetericide or germicide, from 0.1 to 1.0% of an auxiliary suspending agent such as fumed or pyrogenic silica and up to 2% of a perfume, the balance, and at least 30% of the composition being a volatile aerosol propellant. It can be said that the amount of polyalkylene glycol needed to suspend the antiperspirant agent will, in general, be from about 2.5 to about 7.5% by weight of the composition when the amount of antiperspirant agent in the composition is about 3.5% by weight.

Although the amount of polyalkylene glycol needed as the sole liquid suspending agent for the above amount of insoluble antiperspirant agent without assistance from, for example, isopropyl myristate will be about 2.5 to 7.5%, if isopropyl myristate or a similar fatty suspending agent is present in the composition this amount may be reduced although the total amount of suspending agent should remain approximately at the level quoted above. A number of instances of the use of both a polyalkylene glycol and a fatty suspending agent will be found in the Examples.

Set out below in Example 1 is a typical formulation of a prior art aerosol antiperspirant and in Examples 2–17, typical formulations according to the invention. Examples 18 and 19 constitute formulations outside the scope of the present invention, since polyalkylene glycols of the Ucon LB series are coloured and immiscible with water and are thus likely to produce staining.

In the specification all percentages are expressed by weight unless otherwise stated.

Bentone 34 (registered Trade Mark) is a hydrophobic bentonite.

Aerosol 200 (registered Trade Mark) is a pyrogenic silica.

EXAMPLE 1

|  | Wt.% |
|---|---|
| Aluminium chlorhydrate | 2.0 |
| Hexachlorophene | 0.2 |
| Bentone = 34 | 0.3 |

|  | Wt.% |
|---|---|
| Isopropyl myristate | 6.0 |
| Trifluorotrichloroethane | 12.6 |
| Tetrafluorodichloroethane | 65.0 |
| Difluorodichloromethane | 14.0 |

EXAMPLE 2

|  |  |
|---|---|
| Aluminium chlorhydrate | 3.50 |
| Hexachlorophene | 0.10 |
| Aerosil 200 | 0.50 |
| Isopropyl myristate | 4.77 |
| Pluronic L 121 | 1.50 |
| Perfume | 0.40 |
| Fluorotrichloromethane/difluorodichloromethane (70/30) | 89.23 |

EXAMPLE 3

Pluronic L 121 in the formulation of Example 2 was replaced by 1.50% of Pluronic L 62D.

EXAMPLE 4

Pluronic L 121 in the formulation of Example 2 was replaced by 1.50% of Pluronic L 64.

EXAMPLE 5

Pluronic L 121 and isopropyl myristate in the formulation of Example 2 were replaced by 6.27% of Pluronic L 62D.

EXAMPLE 6

Pluronic L 121 and isopropyl myristate in the formulation of Example 2 were replaced by 6.27% of Ucon 50-HB-660.

EXAMPLE 7

Puloronic L 121 and isopropyl myristate in the formulation of Example 2 were replaced by 6.27% of Ucon HB-2000.

EXAMPLE 8

Pluronic L 121 and isopropyl myristate in the formulation of Example 2 were replaced by 6.27% of Ucon HB-3520.

EXAMPLE 9

Pluronic L 121 and isopropyl myristate in the formulation of Example 2 were replaced by 6.27% of polypropylene glycol 2025.

EXAMPLE 10

Pluronic L 121 and isopropyl myristate in the formulation of Example 2 were replaced by 6.27% of polypropylene glycol 1025.

EXAMPLE 11

Pluronic L 121 and isopropyl myristate in the formulation of Example 2 were replaced by 6.27% of polypropylene glycol 425.

EXAMPLE 12

|  | % |
|---|---|
| Aluminum chlorhydrate | 3.50 |
| Hexachlorophene | 0.10 |
| Aerosil 200 | 0.50 |
| Ucon 50-HB-660 | 4.77 |
| Pluronic L 64D | 1.50 |
| Perfume | 0.40 |
| Propellant 11/12 ratio 70/30 | 89.25 |

EXAMPLE 13

Ucon 50-HB-660 in the formulation of Example 12 was replaced by 4.77% of Ucon 50-HB-2000.

EXAMPLE 14

Ucon 50-HB-660 in the formulation of Example 12 was replaced by 4.77% of Ucon 50-HB-3520.

EXAMPLE 15

Ucon 50-HB-660 in the formulation of Example 12 was replaced by 4.77% of polypropylene glycol 425.

EXAMPLE 16

Ucon 50-HB-660 in the formulation of Example 12 was replaced by 4.77% of polypropylene glycol 1025.

EXAMPLE 17

Ucon 50-HB-660 in the formulation of Example 12 was replaced by 4.77% of polypropylene glycol 2025.

EXAMPLE 18

Pluronic L 121 and isopropyl myristate in the formulation of Example 2 were replaced by 6.27% of Ucon LB-1800-X.

EXAMPLE 19

Ucon 50-HB-660 in the formulation of Example 15 was replaced by 4.77% of Ucon LB-1800-X.

A laboratory test devised to reproduce the type of staining observed during the normal use of aerosol powder suspension antiperspirants will now be described.

TEST

The aerosol product being tested is sprayed onto the centre of a 10 × 20 cms cotton sheet for 5 seconds. The sheet is kept at room temperature for 24 hours, then added to a 6 to 9 1b charge of dirty domestic washing and washed in a domestic washing machine using an anionic-based synthetic detergent powder such as Surf or Omo (registered Trade Marks). The sheet is then dried and ironed. This process is repeated until staining occurs.

A product with a marked staining potential shows staining after 5-6 appplications. A product with a low staining potential shows no staining after 20 applications.

Aerosol antiperspirants sold in South Africa under the registered Trade Marks "Right Guard", "Shields" and "Arrid" showed staining after from 1 to 5 applications. However none of the Examples according to the invention showed staining after 5 applications and many showed none even after 10 applications. If the Examples are arranged in order of staining the heaviest stainers appear on the left, as follows:

1,18 and 19 > 2 > 3,4 > 5 > 6–12 > 13 > 14–17

It can be seen that the compositions according to the invention provide a marked improvement in the level of staining over the prior art compositions and over the compositions containing surfactants other than those specified.

In a modification of the invention, the polyalkylene glycol may be replaced wholly or partly by a nonionic surfactant. Examples of such surfactants that we have found to be effective in reducing staining on clothing caused by repeated contact with antiperspirants are polyoxyethylene stearates such as: Myrj 52 (Trade Mark), supplied by Atlas Chemical Industries, nonyl phenolethylene oxide condensates such as Nonidet P80 (Trade Mark) supplied by Shell Chemicals Ltd and ethoxylated lanolins such as Solulan (Trade Mark).

Three examples of compositions according to the above modification of the invention follow:-

EXAMPLE 20

|  | Wt.% |
| --- | --- |
| Aluminium chlorhydrate | 3.50 |
| Hexachlorphene | 0.10 |
| Aerosil 200 | 0.50 |
| Isopropyl myristate | 4.77 |
| Myrj 52 | 1.50 |
| Perfume | 0.40 |
| Fluorotrichloromethane/difluorodichloromethane 70/30 | 89.23 |

EXAMPLE 21

Myrj 52 in the formulation of Example 20 was replaced by 1.50% of Nonidet P80.

EXAMPLE 22

Myrj 52 and isopropyl myristate in the formulation of Example 2 were replaced by 6.27% of Nonodet P80.

Example 20 and Examples 21 and 22 produced staining on clothing at about the same levels as Example 3 and Example 5 respectively and so exhibit a significant improvement over the prior art.

We claim:

1. In an antiperspirant composition comprising a suspension of from 0.1 to 10% by weight of a finely divided aluminium chlorhydrate in a solution containing isopropyl myristate and a halogenated hydrocarbon aerosol propellant selected from the group consisting of difluorodichloromethane, fluorotrichloromethane, tetrafluorodichloroethane, trifluorotrichloroethane and mixtures thereof, the improvement which comprises replacing the isopropyl myristate with a colorless, water- and propellant-miscible compound having the general formula $$C_4H_9(OC_nH_{2n})_xOH$$

wherein $n$ is 2 or 3 and $x$ represents the number of moles of ethylene oxide and 1,2-propyleneoxide respectively such that the viscosity of the compound is from about 660 to about 3520 Saybolt Universal Seconds at 100° F, wherein the ratio of the colorless water- and propellant-miscible compound to the aluminium chlorhydrate is such that when the amount of the colorless water- and propellant- miscible compound is from about 2.5 to about 7.5% by weight, the amount of the aluminium chlorhydrate is about 3.5% by weight.

* * * * *

UNITED STATES PATENT AND TRADEMARK OFFICE
CERTIFICATE OF CORRECTION

PATENT NO. : 4,110,428
DATED : August 29, 1978
INVENTOR(S) : Kuhn et al.

It is certified that error appears in the above-identified patent and that said Letters Patent are hereby corrected as shown below:

In the Title Page:

Under the heading, "Related U.S. Application Data", amend the paragraph to read as follows:

-- Continuation of Ser. No. 525,267, Nov. 19, 1974 [1976], abandoned, which is a continuation of Ser. No. 313,906, Dec. 11, 1972, abandoned, which is a continuation-in-part of Ser. No. 124,453, Mar. 15, 1971, abandoned. --

Signed and Sealed this

*Twenty-second* Day of *May 1979*

[SEAL]

*Attest:*

RUTH C. MASON
*Attesting Officer*

DONALD W. BANNER
*Commissioner of Patents and Trademarks*